United States Patent [19]
Grisoni et al.

[11] Patent Number: 5,585,049
[45] Date of Patent: Dec. 17, 1996

[54] METHOD FOR FORMING FIXATION MEMBERS AFTER OPTIC ATTACHMENT

[75] Inventors: Bernard F. Grisoni, Arlington, Tenn.; Christopher E. Doyle, Irvine, Calif.

[73] Assignee: Allergan, Waco, Tex.

[21] Appl. No.: 300,026

[22] Filed: Sep. 2, 1994

[51] Int. Cl.$^6$ ..................................... B29D 11/00
[52] U.S. Cl. .............. 264/1.7; 264/2.7; 264/295; 264/296; 264/339
[58] Field of Search ............ 264/1.7, 2.7, 249, 264/339, 295, 296, 2.5, 1.1; 623/6

[56] References Cited

U.S. PATENT DOCUMENTS

| | | | |
|---|---|---|---|
| 3,072,963 | 1/1963 | Wilhelm et al. | 264/339 |
| 3,154,620 | 10/1964 | De Lise | 264/339 |
| 3,384,695 | 5/1968 | Murray | 264/295 |
| 4,113,088 | 9/1978 | Binkhorst . | |
| 4,149,279 | 4/1979 | Poler . | |
| 4,150,471 | 4/1979 | Richards et al. | 264/249 |
| 4,160,006 | 7/1979 | Patzner et al. | 264/339 |
| 4,173,281 | 11/1979 | Trought . | |
| 4,205,747 | 6/1980 | Gilliam et al. . | |
| 4,257,521 | 3/1981 | Poler . | |
| 4,268,921 | 5/1981 | Kelman . | |
| 4,269,307 | 5/1981 | LaHaye . | |
| 4,326,306 | 4/1982 | Poler . | |
| 4,328,595 | 5/1982 | Sheets . | |
| 4,402,396 | 9/1983 | Graham . | |
| 4,418,431 | 12/1983 | Feaster . | |
| 4,423,809 | 1/1984 | Mazzocco . | |
| 4,437,194 | 3/1984 | Hahs . | |
| 4,463,457 | 8/1984 | Kelman . | |
| 4,508,216 | 4/1985 | Kelman . | |
| 4,543,673 | 10/1985 | Darke et al. . | |
| 4,684,014 | 8/1987 | Davenport . | |
| 4,759,815 | 7/1988 | Frey | 264/339 |
| 4,993,936 | 2/1991 | Siepser | 264/2.7 |
| 5,185,107 | 2/1993 | Blake | 264/2.5 |

FOREIGN PATENT DOCUMENTS

| | | |
|---|---|---|
| 0069089 | 5/1983 | European Pat. Off. . |
| 0503136 | 9/1992 | European Pat. Off. . |
| 2515956 | 5/1983 | France . |
| 90/04512 | 5/1990 | WIPO . |

OTHER PUBLICATIONS

"An Intraocular Lens Carrier", *American Medical Intra-ocular Implant Society Journal*, Osvaldo I. Lopez, MD et al, vol. 9, No. 4 (Fall 1983), pp. 477–479.

*Primary Examiner*—Mathieu D. Vargot
*Attorney, Agent, or Firm*—Frank J. Uxa

[57] ABSTRACT

A method of making an intraocular lens including attaching a fixation member to an optic to form an IOL assembly with a length of the fixation member between a location on a peripheral surface of the optic and a distal end of the fixation member being elongated and substantially straight. The substantially straight length of the fixation member is permanently deformed into a curved configuration suitable for implantation in an eye of a patient.

6 Claims, 3 Drawing Sheets

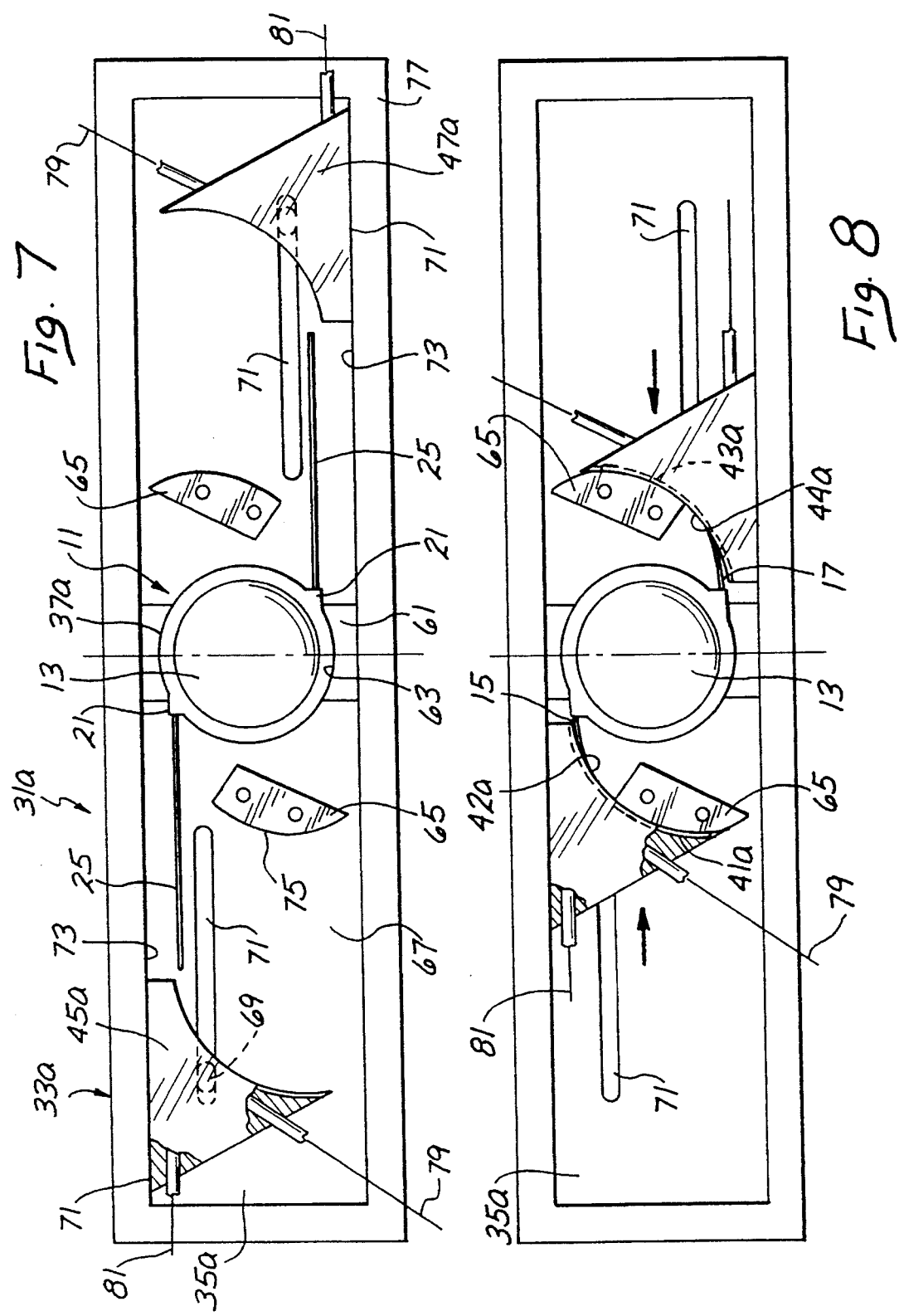

METHOD FOR FORMING FIXATION MEMBERS AFTER OPTIC ATTACHMENT

FIELD OF THE INVENTION

This invention relates to the field of intraocular lens and more particularly to a method and tooling for forming of the fixation members of the intraocular lens after they are attached to the optic. The invention also relates to an IOL assembly which can be worked upon by the tooling of this invention.

BACKGROUND OF THE INVENTION

An intraocular lens (IOL) is commonly used to replace the natural lens of the human eye when the condition of the natural lens so warrants. An IOL typically comprises an optic and fixation members. The fixation members are used to retain the optic in the correct optical position within the eye.

In a one-piece IOL, the fixation members and optic are molded as an integral, one-piece unit. In a multiple-piece IOL, the optic and fixation members are formed separately and then attached. In this latter case, each of the fixation members typically is in the form of an elongated strand or filament of a suitable biocompatible, flexible, resilient material such as polypropylene, polyimide or extruded polymethylmethacrylate (PMMA).

The fixation members are provided for the purpose of mounting or fixing the IOL at a suitable location within the eye, such as the capsular bag. As such, it is important that each of the fixation members have a predetermined configuration in order to properly fix the IOL within the eye and to avoid undue stress on the tissue within eye which supports the IOL. Commonly, each of the fixation members has a curved configuration and may, for example, be generally in the form of a C or a J. As used herein, a curved configuration means a configuration which includes a curve but which may or may not be curved throughout its full length.

In one prior art technique, the fixation members are separately formed into the desired curved configuration and the optic is also separately formed. Following this, the proximal ends of the fixation members are attached to the optic at the desired location to form the completed IOL. In another prior art technique, the curved preformed fixation members are attached to the optic in an insert molding operation.

SUMMARY OF THE INVENTION

This invention provides a method which reduces the cost of manufacturing IOL's. The tooling used in the method is less expensive than the insert molds used previously. The invention also provides an IOL assembly which can be worked upon to provide an IOL.

According to the method of this invention, a fixation member is attached to an optic to form an IOL assembly with a length or region of the fixation member between a location on a peripheral surface of the optic. and a distal end of the fixation member being elongated and substantially straight. The fixation member is also resiliently flexible. The substantially straight length of the fixation member is them permanently deformed into a configuration, and preferably a curved configuration, suitable for implantation in an eye of a patient.

The shaping or forming of the fixation members after attachment to the optic has a number of advantages. For example, the fixation members need only be cut to length and then attached to the optic without any preforming to create a number of IOL assemblies. The substantially straight length of the fixation member of the IOL assembly can then be permanently deformed utilizing relatively inexpensive tooling into any one of a number of desired shapes. Overall, cost is reduced and the particular configuration of the fixation members can be tailored as desired.

Because only the length of the fixation member between a location on the peripheral surface of the optic and the distal end of the fixation member is permanently deformed, the configuration of the proximal end of the fixation member, which is commonly embedded in the optic, is of no consequence to the invention. However, this invention enables filamentary fixation member material to be simply cut to length in an as supplied condition and attached to the optic, and when this is done the entire fixation member may be substantially straight. Also, if the filamentary fixation material is supplied on a reel, it may not be perfectly linear and the term "substantially straight" as used herein is intended to include normal deviations from total linearity than might occur in the as supplied filamentary fixation member material.

The optic may be constructed of a hard, non-deformable material such as PMMA or a soft, resilient deformable material such as a silicone or acrylic materials. The fixation members can be attached to the optic in any conventional manner. This invention is applicable to both non-deformable and deformable optics.

The fixation members of the IOL assembly may be either vaulted or non-vaulted. In either event this invention permanently deforms the fixation members generally in the plane of the optic of the IOL assembly.

This invention is applicable to fixation members of different materials. However, it is particularly applicable to extruded PMMA because it is a thermoplastic which can be permanently deformed at relatively low temperatures. Polypropylene is a more difficult material to deform because higher temperatures are needed, and it is important to avoid damaging the optic with elevated temperatures during the forming of the fixation members.

The tooling can advantageously include a base having a retainer for holding an optic of the IOL assembly at an optic retention location and first and second shaping members on one side of the optic retention location. One of the shaping members may be integral with the base or a separate member mounted on the base. The shaping members are sized to shape a fixation member of the IOL assembly. The first shaping member has a first fixation member shaping surface which can advantageously be or include an elongated groove sized to receive the fixation member. The shaping members are relatively movable from a first position in which the IOL assembly can be placed on the base with the optic at the optic retention location. This relative movement is along a path to move the fixation member toward the fixation member shaping surface to a holding position in which the fixation member is held against, and in substantial conformity with, the fixation member shaping surface. Tooling of this kind is relatively inexpensive and the particular shape of the fixation member can be controlled by the configuration of the fixation member shaping surface.

In order to shape the fixation member, the fixation member must be heated, and this can be brought about, for example, by placing the base in an oven or by passing a fluid at an elevated temperature through fluid passages in one or both of the shaping members.

In one preferred form, the first fixation member has a curved surface and the groove is in the curved surface. The second shaping member has a curved surface which is of substantially the same configuration as the first fixation member shaping surface. The curved surface of the second shaping member confronts the curved surface of the first shaping member and holds the fixation member in the groove in the holding position. In this form of the invention, the first and second fixation member shaping surfaces are relatively movable toward each other from the first position to the holding position. Preferably the first fixation member shaping surface is fixed with respect to the base.

In a second preferred construction, the second shaping member includes a post mounted for movement relative to the base generally transverse to the direction of elongation of the groove. The post has a sloped camming surface which cams the length of the fixation member against the fixation member shaping surface and a holding surface which holds the length of the fixation member against the fixation member shaping surface.

The deforming of the substantially straight length of the fixation member is preferably carried out by placing the IOL assembly on a base having a fixation member shaping surface which is of substantially the desired curved configuration. Such length of the fixation member is then held against the fixation member shaping surface and is heated to enable it to be permanently reshaped to the desired curved configuration. Following this the fixation member is cooled. In the case of a thermoplastic, the heating and subsequent cooling sets the fixation member in the curved configuration. The holding step may include camming the substantially straight length of the fixation member against the fixation member surface or simply moving such length against the fixation member shaping surface. The step of camming may be carried out by the sloped cam surface of the post and the step of holding may be carried out either with the holding surface of the post or with a movable member which forces the substantially straight length of the fixation member against the fixation member shaping surface.

The invention, together with additional features and advantages thereof may best be understood by reference to the following description taken in connection with the accompanying illustrative drawings.

BRIEF DESCRIPTION OF THE DRAWINGS

FIG, 1 is a perspective view of an IOL assembly constructed in accordance with the teachings of this invention.

FIG. 7 is top plan view of another set of tooling that can be used to convert the IOL assembly of FIG. 1 into the IOL of FIG. 2.

FIG. 8 is a view similar to FIG. 7 with the movable members in the holding position,

DESCRIPTION OF THE PREFERRED EMBODIMENT

Figure 1:
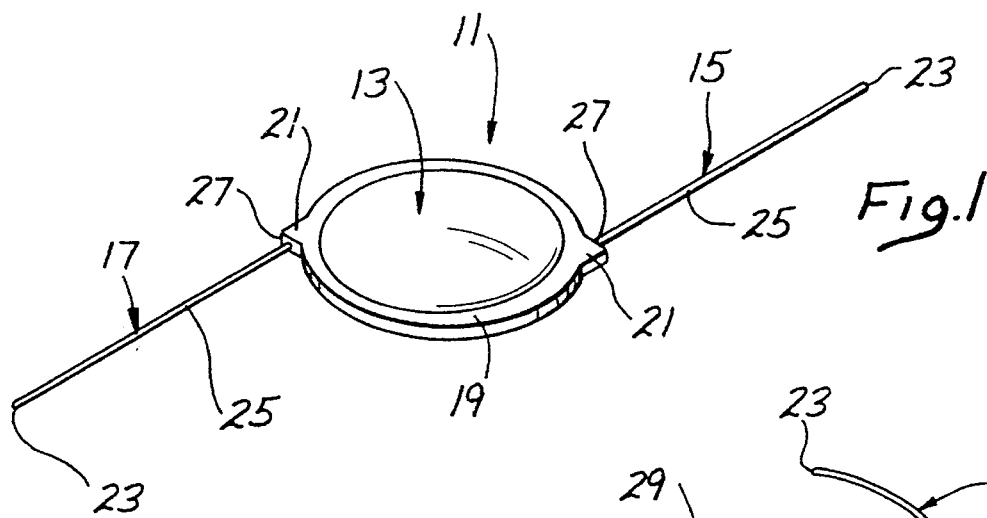

FIG. 1 shows an IOL assembly 11 which generally comprises an optic 13 and identical fixation members 15 and 17. Because the fixation members 15 and 17 are identical, corresponding reference numerals are utilized for corresponding parts, and only the fixation member 15 is described in detail. Although the optic 13 may be deformable or non-deformable, in this embodiment, it is deformable and constructed of a silicone material. The optic has a peripheral surface 19 which is the entire outside surface of the optic. Although the optic 13 may of various different shapes, in this embodiment it is essentially round in plan view except for diametrically opposed mounting tabs 21.

The fixation member 15 is in the form of a fine filament or strand of extruded PMMA. The fixation member is elongated and resiliently flexible such that if it is deflected from the position shown in FIG. 1, it has a memory which returns it essentially to the position shown in FIG. 1. In this embodiment, the fixation members 15 and 17 are constructed of extruded PMMA.

The fixation member 15 has a distal end 23. The fixation member 15 is coupled to the optic 13 and has a length or region 25 which extends from a location 27 on the peripheral surface 19 of the optic 13 to the distal end 23 of the fixation member. The length 25 of the fixation member 15 is substantially straight, and it extends away from the optic. In the embodiment of FIG. 1, the lengths 25 of the fixation members 15 and 17 are not vaulted and lie essentially in the plane of the optic 13. The lengths 25 of the fixation members 15 and 17 are essentially parallel, and even if they were to be in a vaulted construction, would preferably appear generally parallel as viewed in a top plan view. The locations 27 are diametrically opposed.

The fixation member 15 has a proximal end portion (not shown) which is embedded in the optic 13 and in particular the associated mounting tab 21. In this embodiment, the proximal end portion of the fixation member 15 is also substantially straight and aligned with the length 25 of the fixation member 15.

The fixation member 15 can be attached to the optic 13 in any known manner. In the embodiment illustrated, the attachment is made by forcing the proximal end portion of the fixation member 15 into a hole formed in the optic and appropriately adhering the fixation member in the hole substantially as shown and described in common assignee's copending application Ser. No. 08/143,798 filed on Oct. 27, 1993. Of course, any of the known techniques for making this attachment can be employed.

Figure 2:
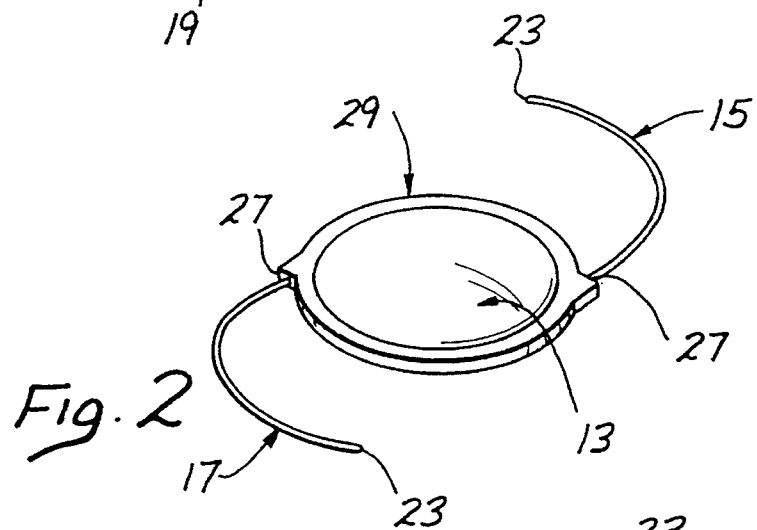
FIG. 2 is a perspective view of an intraocular lens.
Figure 3:
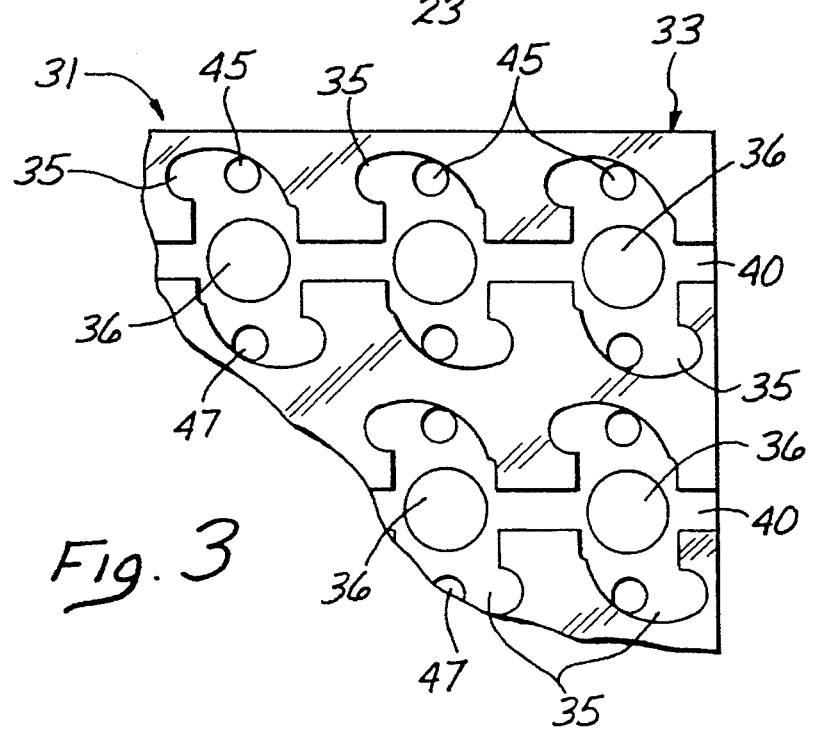
FIG. 3 is a fragmentary plan view of one form of tooling which can be used to convert the IOL assembly of FIG. 1 into the intraocular lens of FIG. 2.

The IOL assembly 11 can be converted into an IOL 29 (FIG. 2). Portions of the IOL 29 corresponding to portions of the IOL assembly 11 are designated by identical references numerals. The only difference between the IOL 29 and the IOL assembly 11 is that the fixation members 15 and 17 of the IOL have, in the form shown in FIG. 2, a curved configuration suitable for implantation in an eye of a patient. In the form shown in FIG. 2, the curved configuration is generally a C-shaped configuration, although any other configuration suitable for implantation in an eye of a patient can be provided.

Figure 4:
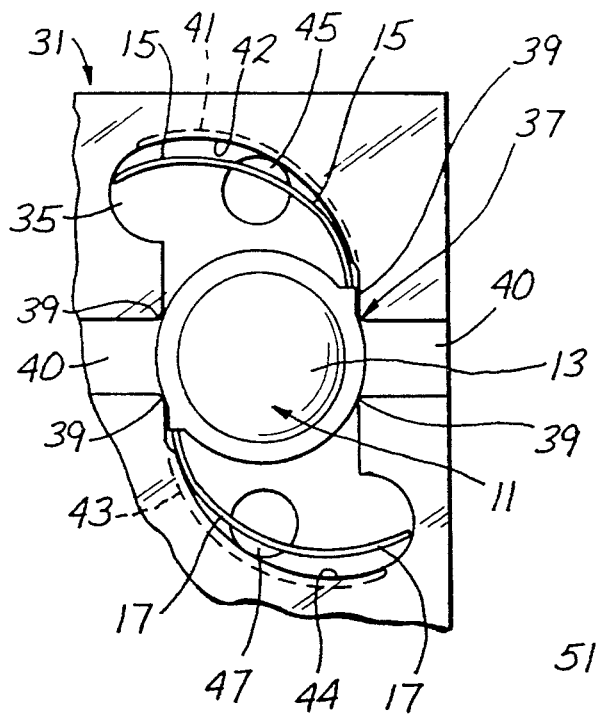
FIG. 4 is an enlarged fragmentary plan view illustrating one cavity of the tooling of FIG. 3 with an IOL assembly retained in the cavity.
Figure 5:
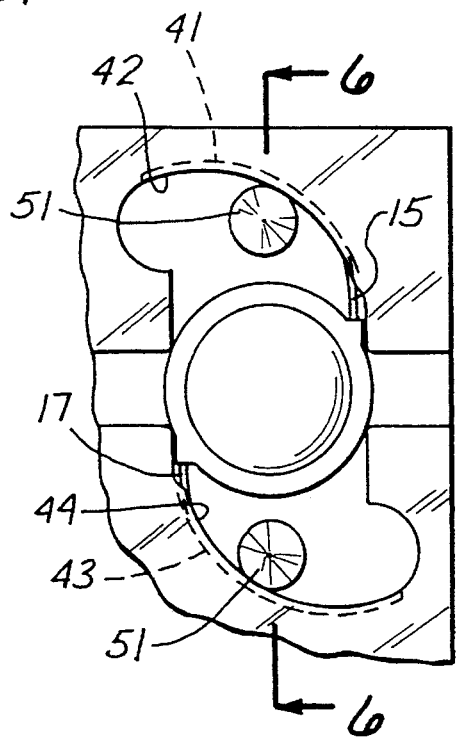
FIG. 5 is a view similar to FIG. 4 with the posts in the holding position.
Figure 6:
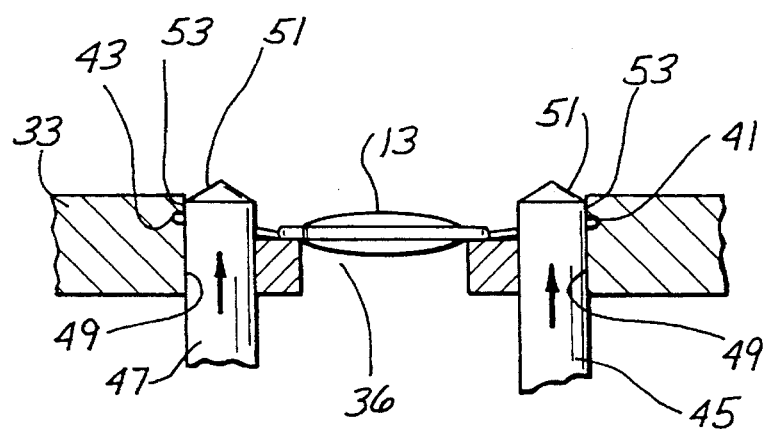
FIG. 6 is a fragmentary sectional view taken generally along line 6—6 of FIG. 5.

To form the IOL 29 from the IOL assembly 11, it is necessary to permanently deform the substantially straight lengths 25 of the fixation members 15 and 17 into configurations suitable for implantation in an eye of a patient. This can be accomplished in various ways including by use of tooling 31 of FIGS. 3–6. The tooling 31 includes a base 33 which has a plurality of cavities 35 each of which is sized to receive an IQL assembly, such as the IOL assembly 11. Each of the cavities 35 may be identical, and one of them is described in greater depth in connection with FIGS. 4–6. The cavity has an opening 36 adapted to be beneath the optic 13 as shown in FIG. 6. The cavity 35 of FIGS. 4–6 has a retainer 37 for holding the optic 13 of the IOL assembly 11 at an optic retention location in the cavity 35. Although the retainer 37 can be of any construction which will carry out this purpose, in this embodiment, it includes four shoulders 39 engagable with the optic 13 to maintain it at the optic retention location as best seen in FIGS. 4 and 5. The shoulders 39 are defined by the intersection of a groove 40, which extends for the full length of the base 33, and the cavity 35.

The base 33 has fixation member shaping surfaces in the form of elongated grooves 41 and 43 sized to receive the fixation members 15 and 17, respectively, and formed in curved surfaces 42 and 44, respectively, of the base 33 on opposite sides of the optic retention location. Although the shaping surfaces 42 and 44 could be defined by a separate member within the base, in this embodiment it is preferred to have the shaping surfaces defined by the base itself, and thus the base 33 may considered as including two integral shaping members defining the surfaces 42 and 44, respectively. Each of the grooves 41 and 43 and each of the surfaces 42 and 44 has a curved configuration conforming to the desired curved configuration for an associated fixation member 15 and 17. In this embodiment each of the curved configurations of the shaping surfaces 41 and 43 is generally C-shaped.

The tooling 31 also includes identical movable shaping members 45 and 47, each of which in this embodiment is in the form of a post. Each of the shaping members 45 and 47 are mounted in bores 49, respectively of the base 33 such that they can move relative to the base generally transversely to the direction of elongation of the associated grooves 41 and 43 as viewed in plan (FIG. 5). More specifically, the bores 49 are closely adjacent the associated surfaces 42 and 44.

Each of the shaping members 45 and 47 has a sloped cam surface 51 which, in this embodiment, is a conical surface at one end of the shaping member. In addition, each of the shaping members 45 and 47 has a holding surface 53 which, in this embodiment, is a cylindrical surface. Thus, each of the shaping members 45 and 47 may be identical with each of them being in the form of a cylindrical post or rod having a conical end.

In use of the tooling 31 for reshaping of the fixation members 15 and 17 of the IOL assembly 11, the IOL assemblies are placed in the cavities 35, and this done with the movable shaping members 45 and 47 in an initial or lower position in which they do not project into, or significantly into, the cavities 35. In order to place the IOL assemblies 11 into the cavities 35, it is necessary to resiliently deflect the fixation members 15 and 17 as shown by way of example in FIG. 4.

Next, the movable shaping members 45 and 47 are moved upwardly (as viewed in FIGS. 3–6) along paths in which the cam surfaces 51 are closely adjacent the associated surface 42 and 44 to cam the associated fixation member 15 and 17 toward the adjacent groove 41 or 43. In this example, the fixation members 15 and 17 are cammed into the grooves 41 and 43. The paths along which the shaping members 45 and 47 are moved are generally transverse to the direction of elongation of the grooves 41 and 43. The movable shaping members 45 and 47 are moved to a holding position (FIGS. 5 and 6) in which the holding surfaces 53 are closely adjacent the associated surface 42 and 44 to hold the fixation members 15 and 17 in the grooves 41 and 43, respectively. If desired, the movable shaping members 45 and 47 can be coupled together as shown schematically in FIG. 6 by the phantom lines so that all of the movable shaping members of the tooling 31 can be moved together to the holding position either manually or with automated equipment.

The base, with the movable shaping members 45 and 47 in the holding position is then placed into an oven (not shown) and heated to a temperature sufficient to enable the length 25 of all the fixation members to be reshaped into the curved configuration defined by the shaping surfaces 41 and 43. Consequently, upon cooling the fixation members are permanently set in the configuration shown in FIG. 2. For example, for fixation members 15 and 17 of extruded PMMA and an optic 13 of silicone, the IOL assemblies 11 may be heated to a temperature of 80° C. for a period of 15 minutes. The cooling may be accomplished at room temperature. Following cooling, the movable shaping members 45 and 47 are moved back to the initial position of FIG. 4 and the IOL's 29 are removed from the cavities 35.

FIGS. 7 and 8 show tooling 31a for reshaping of the fixation members 15 and 17 of the IOL assembly 11 to form the IOL 29. Portions of the tooling 31a corresponding to portions of the tooling 31 are designated by corresponding references numerals followed by the letter "a".

The tooling 31a includes a base 33a having a cavity 35a. Although only one cavity 35a is shown, the base 33a may comprise multiple cavities, if desired. The base has a retainer 37a for holding the optic 13 of the IOL assembly 11 at an optic retention location. In this embodiment, the retainer 37a comprises a block 61 in the cavity 35a having a cutout region 63 for receiving the optic 13 and for bearing against the mounting tabs 21 to prevent rotation of the IOL assembly 11.

In this embodiment, the fixation member shaping surfaces, i.e. the grooves 41a and 43a are provided by movable shaping members 45a and 47a mounted on the base 33a within the cavity 35a. The tooling 31a includes fixed shaping members 65 suitable mounted on the base 33a in the cavities 35a on opposite sides of the optic retention location. The fixed shaping members 65 may be integral with the base 33a, if desired, and may or may not be considered as part of the base.

The movable shaping members 45a and 47a differ from the post-like movable shaping members of FIGS. 3–6. The shaping members 45a and 47a are in the form of blocks which slide along a floor 67 of the base 33a toward and away from the fixed shaping members 65. For example, each of the movable shaping members 45a and 47a may have a tab 69 which rides in a slot 71 in the floor 67 with a flat side 71 of the shaping member sliding along a flat peripheral wall 73. As shown in FIGS. 7 and 8 the shaping members 45a and 47a are on opposite sides of the optic retention location defined by the retainer 37a.

The movable shaping members 45a and 47a each have curved surfaces 42a and 44a in which the curved grooves 41a and 43a are formed. The fixed shaping members 65 have curved surfaces 75 which generally conform to the curvature of the surfaces 42a and 44a, respectively.

In use of the tooling 31a, an IOL assembly 11 is placed in the cavity 35a with the movable shaping members 45a and 47a in an initial position shown in FIG. 7 in which they are sufficiently removed from the associated fixed shaping member 65 so as not to significantly inhibit placement of the IOL assembly into the cavity. Next, the movable shaping members 45a and 47a are moved along a path toward the fixed shaping members 65. The curved surfaces 42a and 44a contact the lengths 25 of the fixation members and the lengths 25 enter the associated grooves 41a and 43a. This movement of the movable shaping members 45a and 47a along a path defined by the groove 71 and peripheral wall 73, moves or deflects the lengths 25 of the fixation members into the grooves 41a and 43a. Movement of the movable shaping members 45a and 47a along this path continues until they reach a holding position in which the fixation members are held in the grooves 41a and 43a by the fixed shaping members 65. In the holding position, the surfaces 75 confront and may engage the associated curved shaping surface 42a or 44a. The movement of the movable shaping members 45a and 47a may be accomplished manually or by a suitably powered mechanism.

Next, the IOL assembly 11 is heated in any suitable manner such as by passing a fluid, such as hot air or a heated liquid at an appropriate elevated temperature through fluid passages 77 in the movable shaping members 45a and 47a. If a hot liquid is used, it may be oil or water. The heating temperature and the duration heating may be as described above in connection with the embodiment of FIGS. 3–6. The hot fluid may be supplied by a supply conduit 79 leading from a source (not shown) and returned to the source via a return conduit 81.

Although exemplary embodiments of the invention have been shown and described, many changes, modifications and substitutions may be made by one having ordinary skill in the art without necessarily departing from the spirit and scope of this invention.

We claim:

1. A method of making an intraocular lens comprising:

attaching a fixation member to an optic to form an IOL assembly with a length of the fixation member between a location on a peripheral surface of the optic and a distal end of the fixation member being elongated, substantially straight and generally in the plane of the optic, said fixation member being resiliently flexible;

permanently deforming the substantially straight length of the fixation member into a curved configuration suitable for implantation in an eye of a patient;

the step of deforming including placing the IOL assembly in a base having a fixation member shaping surface of substantially said curved configuration, holding said length of the fixation member against the fixation member shaping surface, heating said length of the fixation member to enable said length of the fixation member to be permanently reshaped to said curved configuration and cooling the fixation member;

said step of holding including camming said length of the fixation member against said fixation member shaping surface; and the step of camming including moving a post having a holding surface and a sloped cam surface relative to the base with the cam surface camming said length of the fixation member against said fixation member shaping surface and the step of holding also including holding said length of the fixation member against the fixation member shaping surface with the holding surface of the post.

2. A method as defined in claim 1 wherein the step of heating is carried out by placing the base in an oven.

3. A method as defined in claim 1 wherein the fixation member is constructed of extruded polymethylmethacrylate.

4. A method as defined in claim 1 wherein the curved configuration is generally C-shaped.

5. A method as defined in claim 1 wherein said length extends from said location to said distal end.

6. A method as defined in claim 1 wherein the curved configuration extends over a major portion of the fixation member.

* * * * *